US00PP08840P

United States Patent [19]

Meilland

[11] Patent Number: Plant 8,840

[45] Date of Patent: Jul. 19, 1994

[54] ROSE PLANT—MEIMODAC VARIETY

[75] Inventor: Alain A. Meilland, Antibes, France

[73] Assignee: The Conard-Pyle Company, West Grove, Pa.

[21] Appl. No.: 119,372

[22] Filed: Sep. 10, 1993

[51] Int. Cl.[5] ..... A01H 5/00

[52] U.S. Cl. ..... Plt./1

[58] Field of Search ..... Plt. 1, 26

*Primary Examiner*—Howard J. Locker

*Attorney, Agent, or Firm*—Burns, Doane, Swecker & Mathis

[57] ABSTRACT

A new and distinct variety of Shrub Rose plant is provided having attractive long-lasting double flowers which are Cardinal Red suffused with Neyron Rose in coloration. The new variety resulted as a spontaneous mutation of unknown causation of the Meidomonac variety U.S. Plant Pat. No. 5,105). The new variety can be readily distinguished from the parent variety in view of its distinctive blossom coloration. The growth habit and the color and texture of the foliage are substantially identical to those of the parent variety. However, the overall plant size, the bloom size, and the foliage size of the new variety tend to be slightly larger than those of the parent variety under the same growing conditions. Commonly, the new variety forms attractive blossoms (as described) on a very abundant and continuous basis, forms vigorous vegetation, is not particularly affected by cryptogamic diseases, and exhibits excellent resistance to frost. The new variety particularly is suited for growing as attractive ornamentation in the landscape.

1 Drawing Sheet

SUMMARY OF THE INVENTION

The new rose variety of the Shrub Class of the present invention was discovered in France as a spontaneus mutation of unknown causation among plants of the Meidomonac variety (U.S. Plant No. 5,105). I was attracted to the new variety primarily because of the distinctive blossom coloration that can be readily distinguished from that of the Meidomonac variety. Had I not discovered and preserved the original plant of the new variety of the present invention it would have been lost to mankind.

As described in U.S. Plant Pat. No. 5,105, the parent Meidomonac variety resulted from the crossing of *Rosa sempervirens* with the Mlle. Marthe Carron variety (non-patented in the United States) to produce a plant that subsequently was crossed with pollen from the Picasso variety (U.S. Plant Pat. No. 3,351).

It was found that the new variety of the present invention forms blossoms that are Cardinal Red suffused with Neyron Rose. These can be contrasted with the Neyron Pink blossoms of the parent Meidomonac variety. The blossoms of the new variety are substantially of the same shape and texture as those of the parent variety.

The growth habit and the color and texture of the foliage of the new variety are substantially identical to those of the Meidomonac variety. However, it commonly is found that the bloom size, the leaf size, and the overall plant size are slightly larger than those of the parent variety under the same growing conditions.

The new variety has been found to meet the needs of the horticultural industry for many uses, and has been found to be particularly suited for growing as attractive ornamentation in parks, gardens, public areas, and residential landscapes.

The characteristics of the new variety have been found to be homogeneous and stable to be strictly transmissible by asexual propagation carried out in France (e.g., by budding, grafting, cuttage, etc.) from one generation to another.

The new variety of the present invention has been named the Meimodac variety.

BRIEF DESCRIPTION OF THE PHOTOGRAPH

The accompanying photograph shows as nearly true as it is reasonably possible to make the same in a color illustration of this character, typical specimens of plant parts of the new variety of the present invention obtained from two year old plants grown in greenhouses on their own roots at Le-Cannet-Des-Maures, Var, France.

FIG. 1—illustrates a specimen of a young shoot;

FIG. 2—illustrates a specimen of two buds before the opening of the sepals;

FIG. 3—illustrates a specimen of two buds at the opening of the sepals;

FIG. 4—illustrates a specimen of two buds following the opening of the sepals;

FIG. 5—illustrates a specimen of two flowers during the course of opening;

FIG. 6—illustrates a specimen of an open flower - plan view - obverse;

FIG. 7—illustrates a specimen of an open flower - plan view - reverse;

FIG. 8—illustrates a specimen of an open flower prior to petal drop - plane view - obverse;

FIG. 9—illustrates a specimen of an open flower prior to petal drop - plan view - reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a portion of a flowering stem;

FIG. 13—illustrates a specimen of a portion of a main branch;

FIG. 14—illustrates a specimen of leaves with three leaflets showing the upper and under surfaces;

FIG. 15—illustrates a specimen of leaves with five leaflets showing the upper and under surfaces; and FIG. 16—illustrates a specimen of leaves with seven leaflets showing the upper and under surfaces.

DETAILED DESCRIPTION

Figures 1, 2, 3, 4, 5, 6, 7, 8, 9, 10, 11, 12, 13, 14, 15, 16:
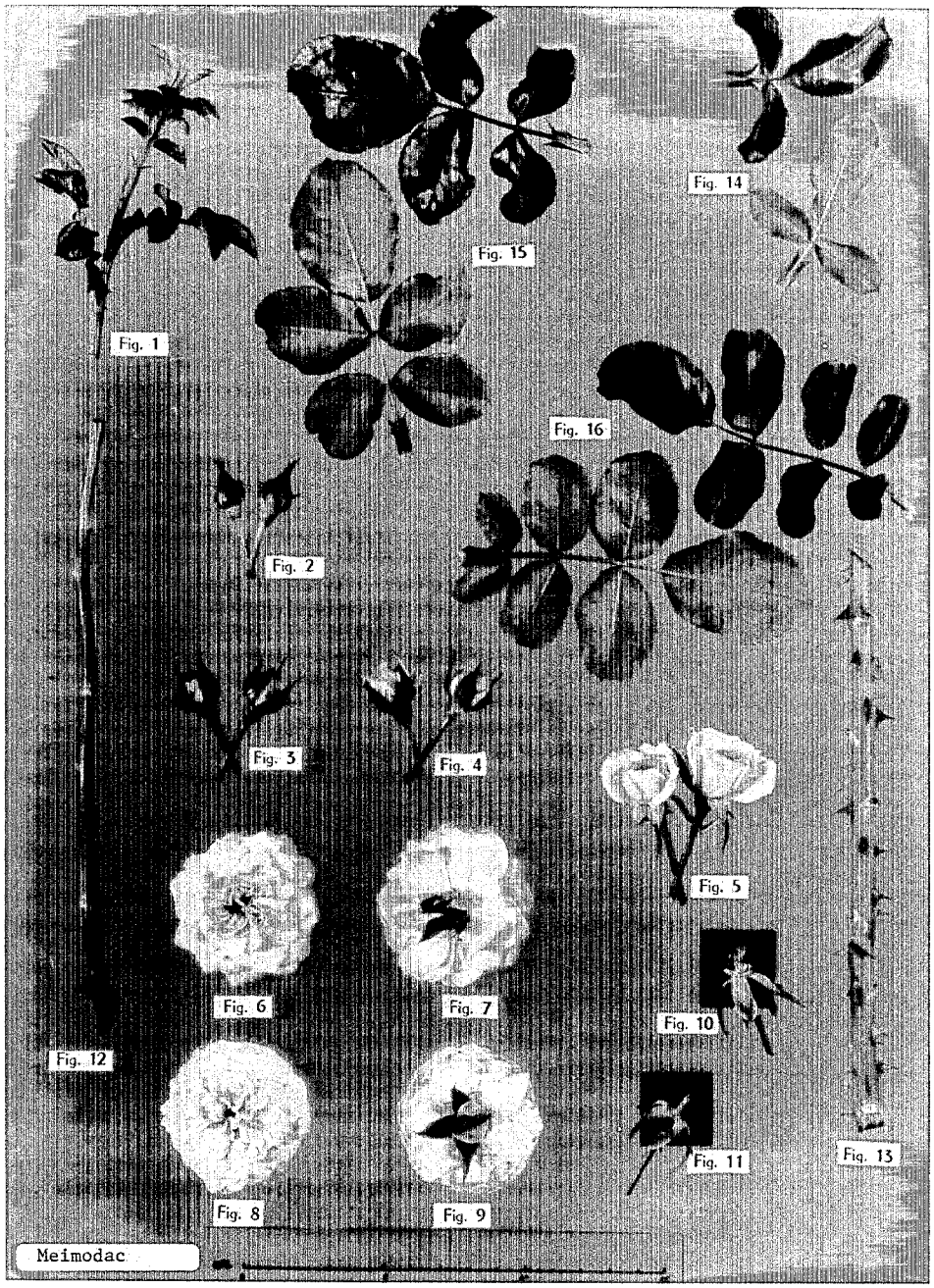

The plants described were two years of age and were grown in greenhouses on their own roots at Le-Cannet-Des-Maures, Var, France. The chart used in the identification of the colors is that of The Royal Horticultural Society (R.H.S. Colour Chart). The terminology preceding the numbered references has been added to designate in common terms, the corresponding colors.

Class: Shrub.

Plant:

*Height.*—Approximately 75 to 80 cm. on the average.

*Habit.*—Bushy.

Branches:

*Color.*—On young stems: light green, Yellow-Green Group 146B, sometimes very lightly shaded with reddish coloration. On mature wood: bronze green, Yellow-Green Group 146A, and bears a few prickles.

Leaves:

*Stipules.*—Adnate, pectinate, rather large and linear.

*Petioles.*—Inner surface: reddish-brown on young foliage, medium green on adult foliage, with more or less glandular edges. Outer surface: light green, and very rarely bears prickles.

*Leaflets.*—Number: 3, 5 (most often), and 7. Shape: oval with narrow tip. Serration: simple and regular. Texture: rough. General appearance: dense and semi-dull. Color of young foliage: Upper surface: dark green, Yellow-Green Group 147A and slightly tinted with reddish coloration. Under surface: medium green, Yellow-Green Group 147B, and slightly tinted with reddish coloration. Color of adult foliage: Upper surface: dark green, Yellow-Green Group 147A. Under surface: medium green, Yellow-Green Group 147B.

Inflorescence:

*Number of flowers.*—Commonly multiflorous with approximately 1 to 20 flowers per stem.

*Peduncle.*—Straight, rigid, extensively tinted with reddish coloration, very glandular, and approximately b 2.5 to 3 cm. in length.

*Sepals.*—Upper surface: tomentose and greenish in coloration. Under surface: light green, more or less tinted with reddish coloration, and more or less glandular. The outer sepals may have edges which are lightly appendiculated.

*Buds.*—Shape: oval before the opening of the sepals. Length: approximately 1.4 cm. on average outside the calyx at the opening of the sepals. Size: small. Color when first opening: Interior surface: Rose Red, Red-Purple Group 58B. Exterior surface: Rose Red, Red-Purple Group 58B.

*Flower.*—Form: double, initially globular, changing to the shape of a cup and finally changing to the shape of a flat cup immediately prior to the petal drop. Diameter: approximately 6 cm. on the average. Color during course of opening: Upper surface: Cardinal Red, Red Group 53B, and more or less suffused with Neyron Rose, Red Group 55A. Under surface: Cardinal Red, Red Group 53B, and more or less suffused with Neyron Rose, Red Group 55A. Color when fully open: Upper surface: Cardinal Red, Red Group 53B, and more or less suffused with Neyron Rose, Red Group 55A. Under surface: Cardinal Red, Red Group 53B, and more or less suffused with Neyron Rose, Red Group 55A. Color immediately prior to petal drop: Upper surface: Cardinal Red, Red Group 53B, and more or less suffused with Neyron Rose, Red Group 55A. Under surface: Cardinal Red, Red Group 53B, and more or less suffused with Neyron Rose, Red Group 55A. Fragrance: none. Lasting quality: long. Petals — Shape: round, sometimes with indented tips. Texture: firm. Number: approximately 53 on average. Petal drop: good. Stamens — Number: approximately 20 on average. Anthers: orange in coloration. Filaments: greenish in coloration. Pistils — Number: approximately 28 on average. Stigmas: whitish. Styles: greenish in coloration, slightly tomentose. Receptacle: light green in coloration at the dehiscence of the anthers, and in longiudinal section is narrow and in the shape of a pitcher.

Development:

*Vegetation.*—Very vigorous.

*Blossoming.*—Very abundant.

*Aptitude to fruit bearing.*—Very good.

*Hardiness.*—Exceptionally good.

*Resistance to diseases.*—Exceptionally good.

I claim:

1. A new and distinct variety of shrub rose plant characterized by the following combination of charateristics:

(a) forms on an abundant and continuous basis attractive double blossoms that are Cardinal Red suffused with Neyron Rose in coloration,
(b) exhibits a bushy growth habit,
(c) forms petals that are firm and detach cleanly,
(d) forms bronze green adult wood,
(e) exhibits exceptional hardiness,
(f) exhibits excellent disease resistance, and
(g) is particularly suited for growing in the landscape as attractive ornamentation;

substantially as herein shown and described.

* * * * *

Meimodac